United States Patent [19]
Van Meir et al.

[11] Patent Number: 5,990,280
[45] Date of Patent: Nov. 23, 1999

[54] GLIOBLASTOMA-DERIVED ANGIOGENESIS INHIBITING FACTOR

[75] Inventors: Erwin Van Meir; H.-J. Su Huang; Webster K Cavenee, all of La Jolla, Calif.

[73] Assignee: Ludwig Institue for Cancer Research, New York, N.Y.

[21] Appl. No.: 08/702,710

[22] PCT Filed: Mar. 3, 1995

[86] PCT No.: PCT/US95/02634

§ 371 Date: Nov. 15, 1996

§ 102(e) Date: Nov. 15, 1996

[87] PCT Pub. No.: WO95/24208

PCT Pub. Date: Sep. 14, 1995

Related U.S. Application Data

[63] Continuation-in-part of application No. 08/207,454, Mar. 7, 1994, Pat. No. 5,807,731.

[51] Int. Cl.⁶ ........................ C07K 14/435; C07K 14/515
[52] U.S. Cl. ........................... 530/350; 530/417; 530/828
[58] Field of Search ..................................... 530/350, 417, 530/828

[56] References Cited

U.S. PATENT DOCUMENTS

| 5,192,744 | 3/1993 | Bouck et al. | 514/8 |
| 5,626,841 | 5/1997 | Gurewich | 424/94.63 |

OTHER PUBLICATIONS

K.M. Dameron et al., "Regulation of an Angiogenesis Inhibitor—by the p53 Tumor Suppressor Gene," Proceedings of the American Association for Cancer Research, vol. 34, p. 542, Abstract 3234, (1993).

K. M. Dameron et al., "Regulation of an Angiogenesis Inhibitor—in Human Fibroblasts by the p53 Tumor Suppressor Gene", Journal of Cellular Biochemistry Supplement, vol. 18C, p. 187, Abstract N 306, (1994).

Van Meir et al., "Analysis of the p53 Gene and Its Expression in—Human Glioblastoma Cells", Cancer Research, vol. 54, pp. 649–652, (1994).

M. Gossen et al., "Tight Control of Gene Expression in Mammalian—Cells by Tetracycline–Responsive Promoters", Proceedings of the National Academy of Science, USA, vol. 89, pp. 5547–5551, (1992).

Erwin G. Van Meir, Release of an Inhibitor of Angiogenesis Upon—Induction of Wild Type p53 Expression in Glioblastoma Cells, Nature Genetics, vol. 8, (1994).

Hupp et al. Cell 71:875–888, 1992.

Sitrin et al. Cancer Research 50:4957–4961, 1990.

Sturzbecher et al. Oncogene 7 (1992) 1513–1523.

Rudinger In "Peptide Hormones" (Jun. 1976)ed. J.A. Parsons, University Park Press, Baltimore, pp. 1–7.

*Primary Examiner*—Anthony C. Caputa
*Assistant Examiner*—Robert C. Hayes
*Attorney, Agent, or Firm*—Fulbright & Jaworski, LLP

[57] ABSTRACT

A glioblastoma-derived angiogenesis inhibiting factor is described. The material is induced in presence of wild type p53, but not by several mutated forms of p53. Various uses of the material are described.

1 Claim, 6 Drawing Sheets

GLIOBLASTOMA-DERIVED ANGIOGENESIS INHIBITING FACTOR

RELATED APPLICATION

This is a continuation-in-part of copending application Ser. No. 08/207,454, filed Mar. 7, 1994, now U.S. Pat. No. 5,807,731.

FIELD OF THE INVENTION

The invention relates to an angiogenesis inhibiting factor. More particularly, the factor (GD-AIF" hereafter), is induced in the presence of wild type p53, but not in the presence of any of the mutant forms of p53 which have been tested. The factor has an apparent molecular weight in its active form of approximately 100 kd and is labile to base and acid.

BACKGROUND AND PRIOR ART

Angiogenesis, the sprouting of new capillaries from small venules, occurs through local degradation of the basement membrane lining the venules followed by migration, alignment and proliferation of endothelial cells toward the angiogenic chemoattractant. Under normal conditions capillary proliferation is tightly controlled in adult tissues and occurs only during the female menstrual cycle in the follicle and corpus luteum, in the placenta during pregnancy, and as a result of bodily injury, such as during wound and fracture repair. A disruption of the balance between stimulatory and inhibitory influences on angiogenesis contributes to a variety of pathological conditions. Persistent angiogenicity occurs in diabetic retinopathy, retrolental fibroplasia, neovascular glaucoma, rheumatoid arthritis, hemangiomas, angiofibromas, psoriasis and atherosclerotic plaques, whereas insufficient capillary growth can result in delayed wound healing, nonhealing fractures, ischemia and fetal growth malformations such as hemifacial microsomia (Folkman et al., Science 235: 442–47 (1987)). Neovascularization is also one of the cardinal features that permit neoplastic progression. Tumor growth is critically dependent on new blood supply, and tumors cannot exceed a few millimeters in diameter in isolated perfused organs where capillary endothelium is degenerated (Folkman et al., Cancer 16: 453 (1963)).

Recent analysis of a variety of human cancers have shown that tumor progression occurs through the sequential deregulation and rearrangement of protooncogenes together with the inactivation of tumor suppressor genes. (Fearon et al, Cell 61: 759–67 (1990)). Whether any of these genetic alterations can trigger the disruption of control of angiogenesis in humans is unclear but at least four plausible scenarios can be envisaged which could result in escape from the factors regulating microvascular quiescence. First, these angiogenic factors may cause increased production of diffusible growth factors and cytokines that may either act directly as angiogenic factors to activate endothelial cells or indirectly through the recruitment of other cells that promotes neovascularization through the secretion of molecules with angiogenic potency. Second, they may cause the synthesis of enzymes that allow angiogenic factors such as bFGF to be released from extracellular matrix storages. Third, they may cause the stimulation of adjacent stromal and capillary endothelial cells to produce enzymes such as stromelysin and collagenase which induce basement membrane and extracellular matrix degradation and therefore, promote angiogenesis by allowing endothelial cell detachment and migration from the parent venules into the perivascular stroma. Finally, they may act to disrupt the local synthesis of physiologic inhibitors of angiogenesis.

Astrocytomas are an attractive model for investigation of the relationship between genes which are mutated during tumor. progression and angiogenesis. They are among the most dramatically neovascularized neoplasms with respect to vasoproliferation, endothelial cell cytology and endothelial cell hyperplasia (Brem et al., J. Natl. Canc. Inst. 48: 347–356 (1972)). The malignant progression of astrocytoma is histopathologically and clinically well characterized (Russell et al., Pathology of Tumors of the nervous system (Edward Arnold, London, 1989)) and this progression toward malignancy is accompanied by a well-documented sequential accumulation of genetic alterations (Cavenee et al., Mutat. Res. 247: 199–202 (1991)). Among these, the earliest known event is mutation of the p53 tumor suppressor gene and elimination of its wild type activity (Nigro et al., Nature 342: 705–708 (1989). Sidransky et al., Nature 355: 846–7 (1992). The p53 gene is the most frequently mutated gene in a diverse range of human tumors (Nigro et al, supra; Sidransky et al., supra; Levine et al., Nature 3561: 453–6 (1991)) and intensive investigations have established its role in checkpoint maintenance during the cell cycle (Lane, Nature 358: 15–16 (1992)), in transactivation of the transcription of other genes (Kern et al., Science 252: 1708–1711 (1991); Weintraub et al., Proc. Natl. Acad. Sci. USA 88: 4570–71 (1991); Ginsberg et al., Proc. Natl. Acad. Sci. USA 88: 9979–9983 (1991); Farmeu et al., Nature 358: 83–6 (1992)) in cell growth control (Baker et al., Science 249: 912–915 (1990); Martinez et al., Genes Dev 5: 151–9 (1991); Diller et al., Mol. Cell Biol. 10: 5772–5781 (1990)), in the response of cells to DNA damage (Kastan et al., Canc. Res. 51: 6304–11 (1991), in control of genomic stability (Yin et al., Cell 70: 937–948 (1992)); Livingstone et al., Cell 70: 923–935 (1992)), and in predisposition to some familial human cancers (Malkin et al., Science 250: 1233–8 (1990); Srivastava et al., Nature 348: 747–749 (1990). Much less attention has been paid to its role in intercellular interactions.

An angiogenesis inhibiting factor produced by glioblastoma cells has now been identified. This factor, abbreviated as "GD-AIF" for convenience, was found following experiments where a wild type p53 coding sequence was placed under the control of a conditionally inducible, tetracycline-regulated, promoter activating system. The GD-AIF is useful in a therapeutic context. Additionally, it provides a method by which the sequence of events leading to mutation of p53 and the onset of tumorigenic transformation can be measured. Since wild type p53 induces or stimulates GD-AIF production and the tested mutated p53 does not, by assaying for GD-AIF and/or by assaying levels of the factor, one may diagnose or study the onset and progression of cancers, such as glioblastoma. Hence GD-AIF may also be considered a diagnostic and prognostic marker for patients believed to be suffering from a cancer, such as glioblastoma.

The invention is described in greater detail in the disclosure which follows.

WT#11–/bFGF: culture medium of a cell line (WT11) grown in the absence of tetracycline, and then mixed with bFGF WT#11+/bFGF: culture medium of WT11 grown in the presence of tetracycline, and mixed with bFGF WT#11 mix: a 50/50 mix of WT11 culture medium grown in the absence of tetracycline, and culture medium of WT11 grown in the presence of tetracycline WT#11–/+: tetracycline added to culture medium after its removal from WT11/–cells WT#11–: the culture medium of the line grown without tetracycline WT#11+: cells grown in the presence of tetracycline.

Similarly for WT1 and WT4 designations.

Figure 3A:
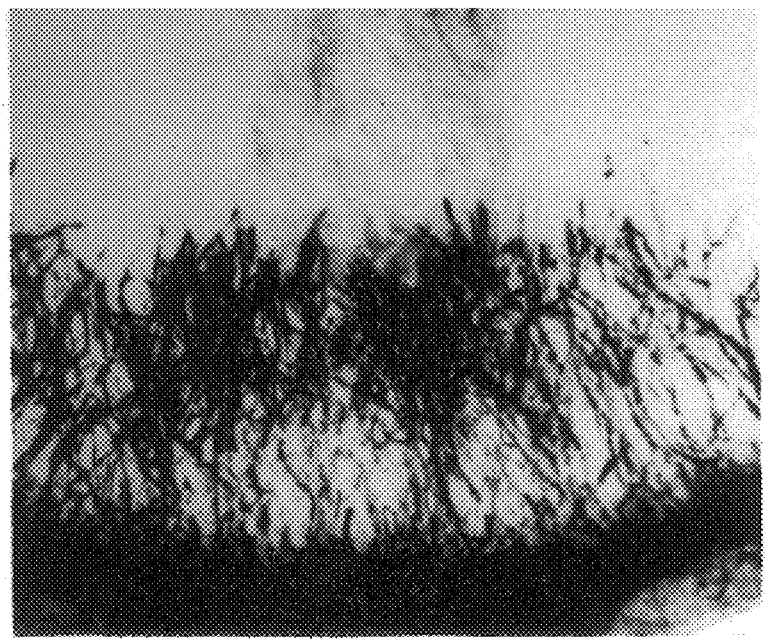
Figure 3B:
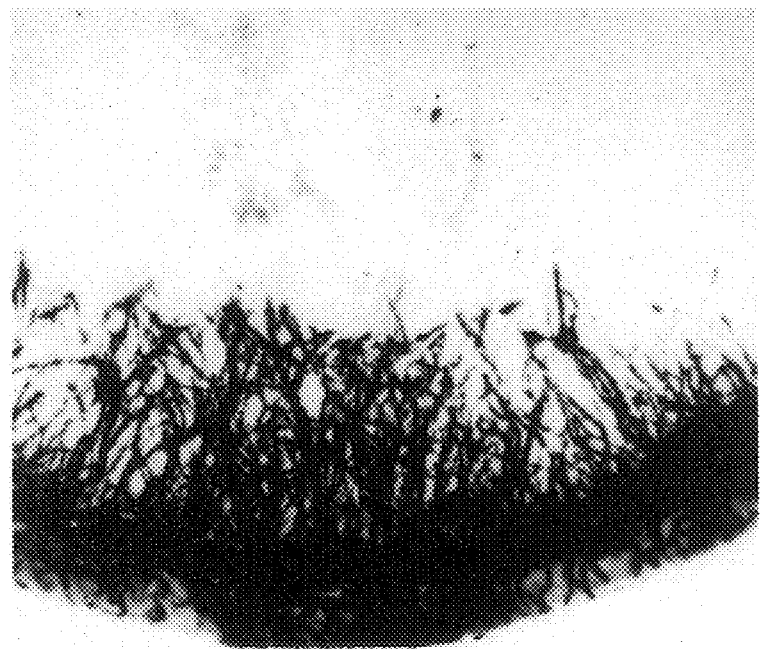

FIGS. 3A-B show two control panels where a HYDRON pellet containing WT–1 culture medium was implanted in a rat cornea. The top panel shows results where the cell line was cultured in the absence of tetracycline, and the bottom, in its presence.

Figure 3C:
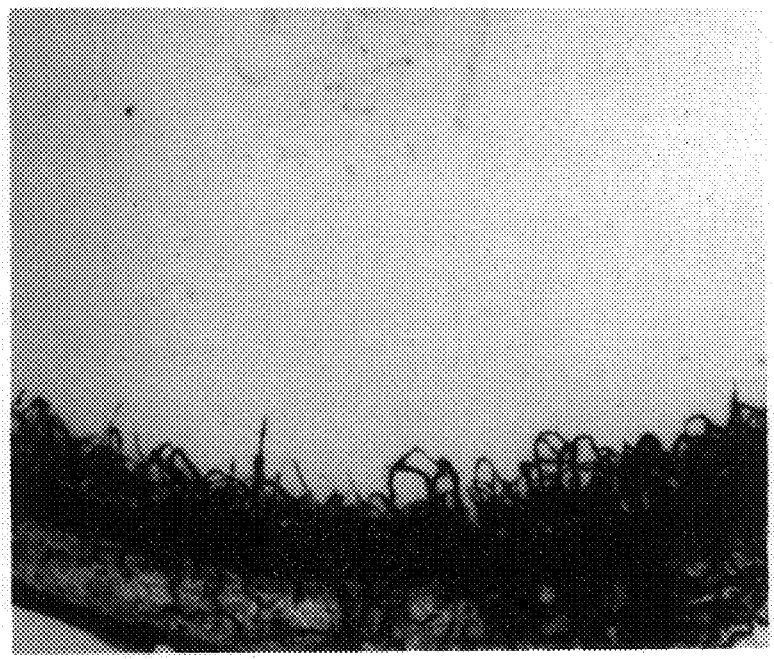
Figure 3D:

FIGS. 3C-D show similar results using WT11 culture medium.

Figure 3E:
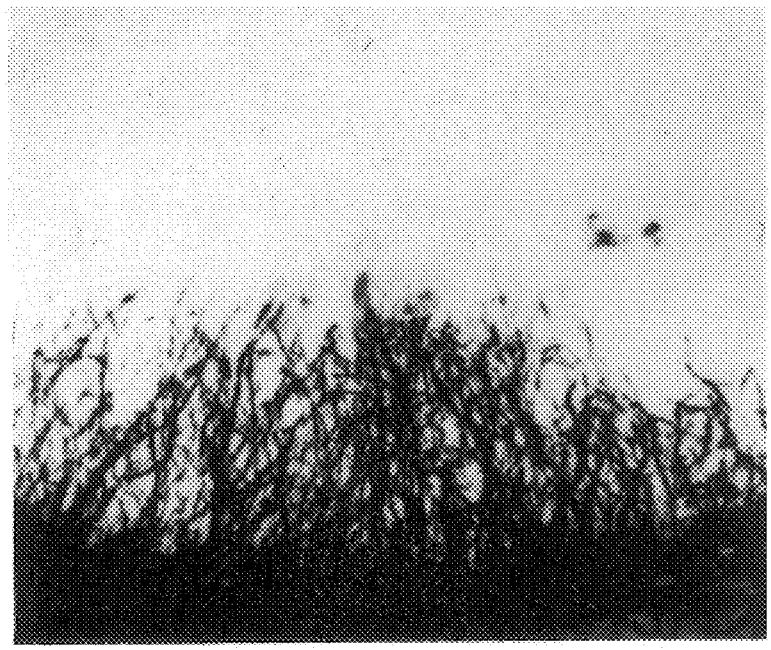
Figure 3F:
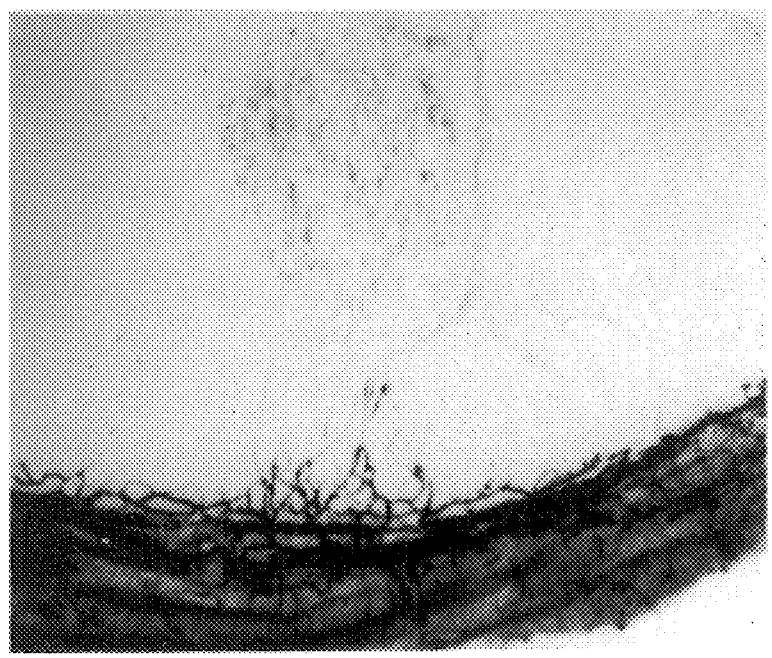

FIGS. 3E-F show results with WT11 culture medium mixed with 25 ng of bFGF.

Figure 3G:
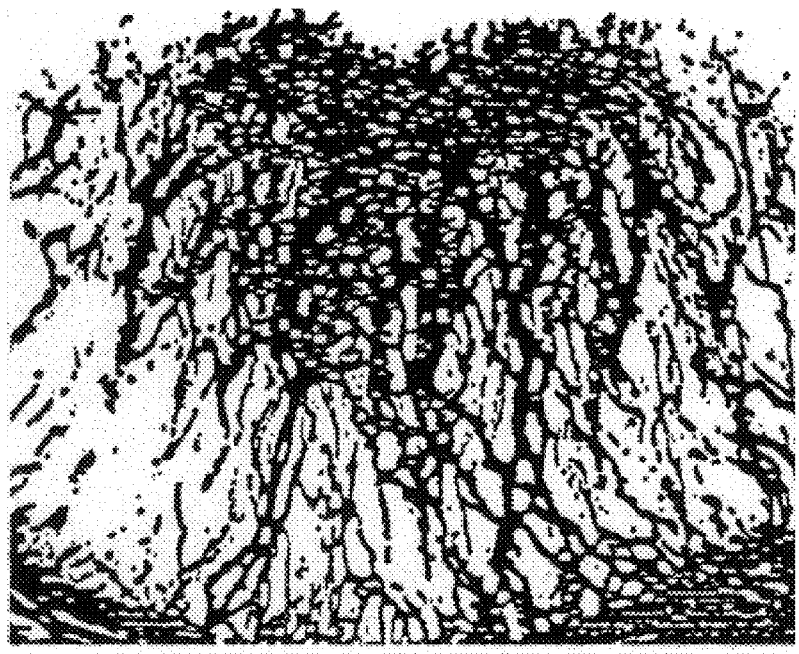
Figure 3H:
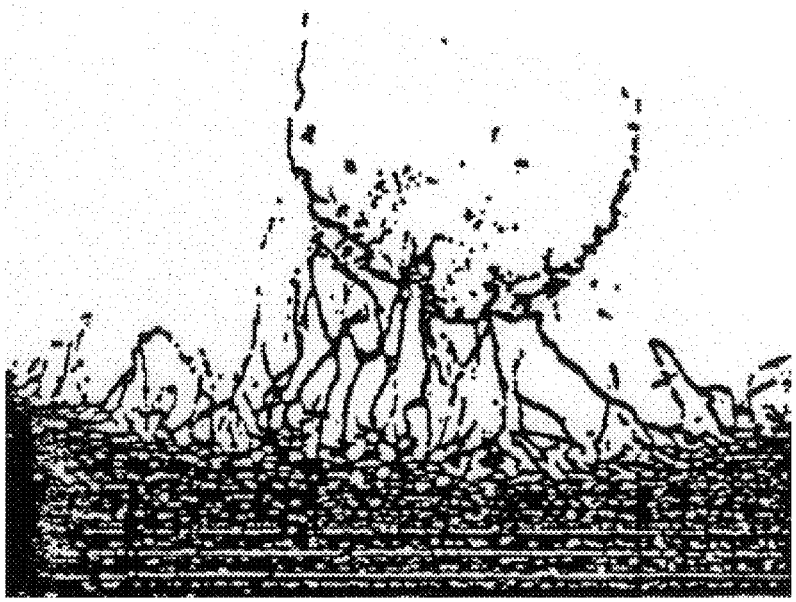

FIGS. 3G-H also show WT4 with (top) and without tetracycline bottom. In the latter, bFGF was added to the culture medium.

DETAILED DESCRIPTION OF PREFERRED EMBODIMENTS

EXAMPLE 1

Glioblastoma cell line LN-Z308 is a cell line which expresses no p53 protein, due to an internal rearrangement of the endogenous p53 gene (Van Meir et a., Canc. Res. 54: 649–52 (1994)). As such, it is an ideal material for the experiments described herein.

First, LN-Z308 cells were transfected with plasmid pUHD15-1 neo (an updated version of pUHD 15-1, described in Gossen & Bujard), using the standard and well known calcium phosphate precipitation method. The plasmid comprises well known elements, including a neomycin resistance gene, and a chimeric gene which encodes a fusion protein of (i) the tetracycline repressor (tetR) of the Tn10 tetracycline resistance operon of *E. coli*, and (ii) the activating domain of virion protein 16 ("VP16") of *Herpes simplex* virus. The fusion protein, referred to hereafter as "tTA", acts as a transactivator that is able to activate transcription of $Ph^{CMV}*$-tetO, which is a combination of a minimal promoter sequence ($P_hCMV*$) derived from the human cytomegalovirus promoter IE, combined with tet operator ("tetO") sequences. See Gossen et al., Proc. Natl. Acad. Sci. USA 89: 5547–5551 (1992), the disclosure of which is incorporated by reference in its entirety. The transfected cells were then selected for neomycin resistance.

The clones which proved to be neomycin resistant were then grown in the absence of tetracycline, and then tested for tetracycline controlled expression of tTA. Specifically, the cells were transiently transfected with pUHC 13-3, which is a reporter construct containing PhCMV*tetO-luciferase. The luciferase reporting system is a well known one, and need not be elaborated upon here. The cells were grown, both in the presence and in the absence of 1 ug/ml tetracycline. In this way, clone LNZTA3 was selected. This clone exhibited a 50–100 fold increase in luciferase activity upon the removal of tetracycline from the growth medium. This clone was used in the experiments which follow, in example 2.

EXAMPLE 2

The clone LNZTA3 was cotransfected with plasmids pUHGp53WT, and pLSHL. Plasmid pUHGp53WT carries a wild type ("WT") p53 gene, under control of PhCMV*tetO, which is described in Example 1. Plasmid pLSHL carries a hygromycin resistance gene. To manufacture pUHGp53WT, an 1800 base pair BamHI restriction fragment of plasmid pC53-SN3 was cloned into the BamHI restriction site of vector pUHG10-3. The first of these plasmids is disclosed in Kern et al., Science 256: 827–30 (1992), and the second is an updated version of pUHD 10-3 described in Gossen et al., supra, both of which are incorporated by reference in their entirety.

The transfected cells were cultured, in the absence (induced) or presence (repressed) of tetracycline (1 ug/ml), for 48 hours, followed by washing and labelling for 90 minutes using serum free medium containing 200 µCi/ml of $^{35}$S-methionine in the presence or absence of tetracycline. The p53 protein expression of the cells was analyzed via immunoprecipitation of cell extracts with a wild type p53 specific antibody, i.e., PAb1601, and electrophoresis on a 10% SDS-PAGE gel, in accordance with Van Meir et al, Canc. Res. 54: 649–52 (1994), incorporated by reference herein.

Figure 1:
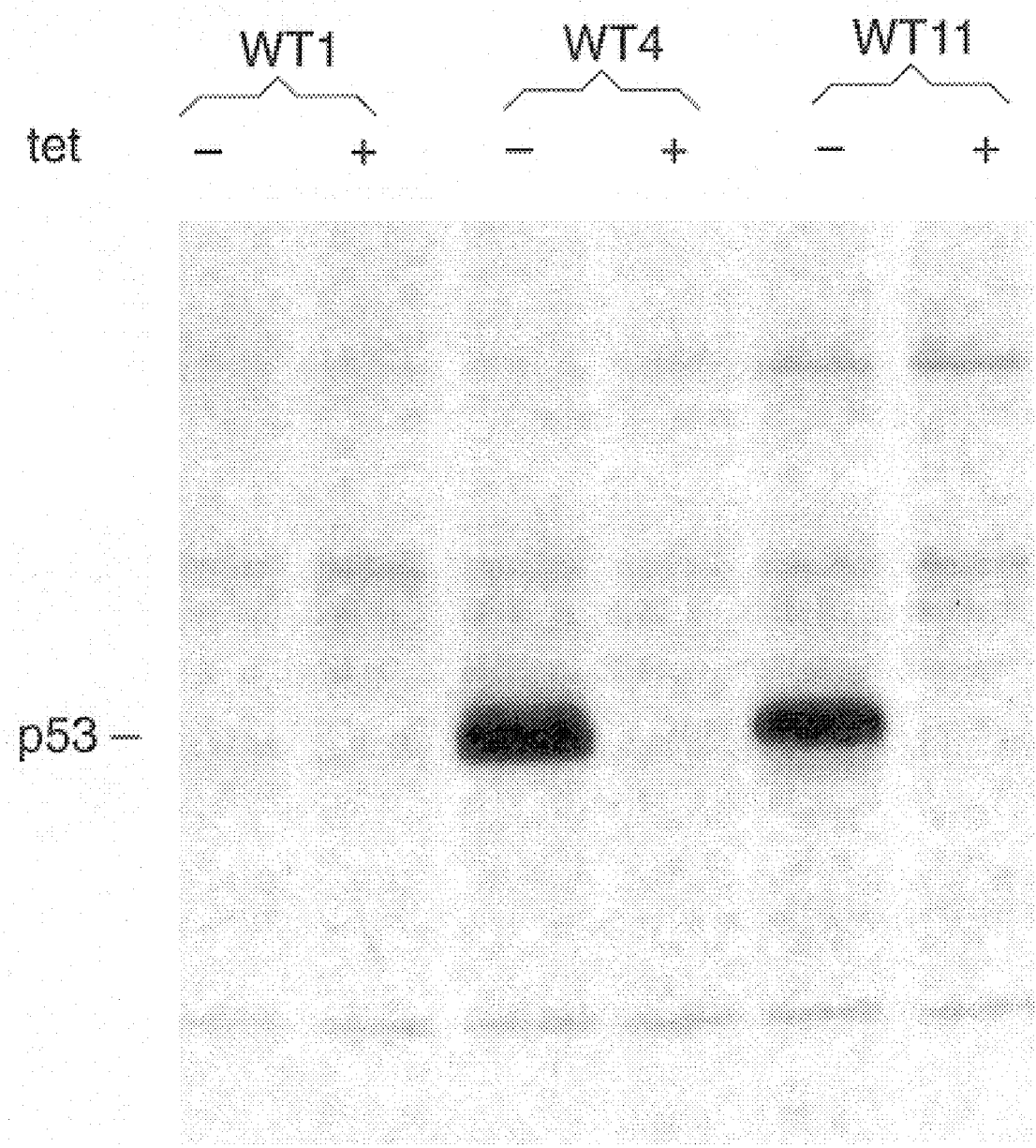
FIG. 1 shows results obtained following immunoprecipitation of cell lysates using a wild type p53 specific antibody. Analysis is on 10% SDS-PAGE gels.

The procedure identified two clones, i.e., LNZTAWT4 and LNZTAWT11, referred to hereafter as "WT4" and "WT11", respectively, which showed undetectable levels of immunoprecipitatable p53 in the repressed state, with substantial increase in the induced state, as can be seen in FIG. 1. A third clone, LNZTA3 WT1 ("WT1") was found which was tTA inducible, but did not express detectable p53 or activity. This cell line served as a control in non-specific aspects of the system.

EXAMPLE 3

Further experiments were carried out to determine if the induced p53 protein had wild type transcriptional and transactivational activity. To do this, plasmids $PG_{13}CAT$ and $MG_{15}CAT$ were transfected, via the calcium phosphate procedure outlined supra, into the WT1, WT4, and WT11 recipient cell lines. $PG_{13}CAT$ carries a minimal polyomavirus early promoter and a gene for chloramphenicol acetyl transferase, located downstream of the "PG" sequence, which confers WT but not mutant p53 binding and transcriptional activation. $MG_{15}CAT$ is a control plasmid carrying a mutated PG element which does not confer transcriptional activation. Kern et al., Science 256: 827–30 (1992), the disclosure of which is incorporated by reference in its entirety, discusses these plasmids in some detail. The cells were cultured, in the absence of tetracycline, for 48 hours, to induce p53 production. The $PG_{13}CAT$ reporter had previously been noted as being specifically responsive to wild type p53 (Kern et al., supra). Forty-eight hours after transfection, cells were scraped from dishes, and lysates prepared. These were tested for CAT activity, with CAT reaction products being separated from the ($^{14}$C) chloramphenicol substrate used, via xylene extraction. The products were counted in a liquid scintillation counter. Results are shown in table 1, which follows. The control used was cells cotransfected with either of $PG_{13}CAT$ and $MG_{15}CAT$, and the transfection control pCMVLuc, a plasmid which constitutively expresses the luciferase gene. The results indicated that the p53 product of WT4 and WT11 was indeed wild type in its activity.

TABLE 1

$PG_{13}CAT$ transactivation assay:

| cells | tet (1 ug/ml) | plasmids | CAT (cpm) | − Background | final cpm. |
|---|---|---|---|---|---|
| WT#1 | − | $PG_{13}CAT$ | 146 | −149 | 0 |
|  | + | " | 142 | −149 | 0 |
| WT#4 | − | " | 739 | −137 | 602 |
|  | + | " | 202 | −137 | 65 |
| WT#11 | − | " | 334 | −162 | 172 |
|  | + | " | 155 | −162 | 0 |
|  |  | = Background: |  |  |  |
| WT#1 | − | $MG_{15}CAT$ | 149 | / | / |
| WT#4 | − | " | 137 | / | / |
| WT#11 | − | " | 162 | / | / |

EXAMPLE 4

The effect of restoration of wild type p53 activity in the angiogenic phenotype of LN-Z308 was tested. To do this, conditioned medium from the parental line (LN-Z308), and the transfected cell lines WT4 and WT11 was prepared. Cells were grown to 80% confluence, washed twice with PBS, and DMEM (without FCS), was left on the cells for 48 hours. The conditioned medium was concentrated about 20 times by centrifugation through filters having a molecular weight cutoff of 3000 daltons. The methodology used was one described by Glaser et al., Nature 288: 483–484 (1980), which is incorporated by reference in its entirety. Specifically, endothelial cell migration across a gelatinized membrane in a modified Boyden chamber was observed.

Parental cell line LN-Z308 is a glioblastoma cell line, and these are known to produce several angiogenic growth factors, including aFGF, bFGF, TGFα, TGFβ, and VEGF (see Gall, in Black et al., ed. Astrocytomas: diagnosis, treatment and biology, Blackwell Scientific Publications, Boston, 1991, pp. 241–249). Thus, first the stimulation of endothelial cell migration in the absence of WTp53 induction was studied (i.e., the glioblastoma cells were cultured in the presence of tetracycline). The conditioned medium of each cell line induced migration to the same extent, and the activity was not increased if bFGF was added to the conditioned medium. The activities were comparable to non-conditioned medium to which bFGF was added.

Experiments were also carried out in which culture medium from WT4 and WT11 grown in the absence of tetracycline, i.e., where WTp53 was induced, was tested for angiogenic effect. Activity levels were strongly reduced. These results suggested one of two conclusions: either p53 caused reduction in the amount of angiogenic factors secreted by the cells, or the elicitation of an inhibitor of the activity.

Additional tests were also carried out. In a first set of experiments, bFGF (25 ng/ml) was added to the conditioned medium, or culture medium from the transfected cells was mixed, equally, with the conditioned medium from the respective clone grown in the absence of tetracycline. Either way, the culture medium from the transfectants inhibited angiogenesis.

In another set of experiments, tetracycline was added after removal of the medium, and during preparation of the medium. Neither approach impacted migration.

Figure 2:
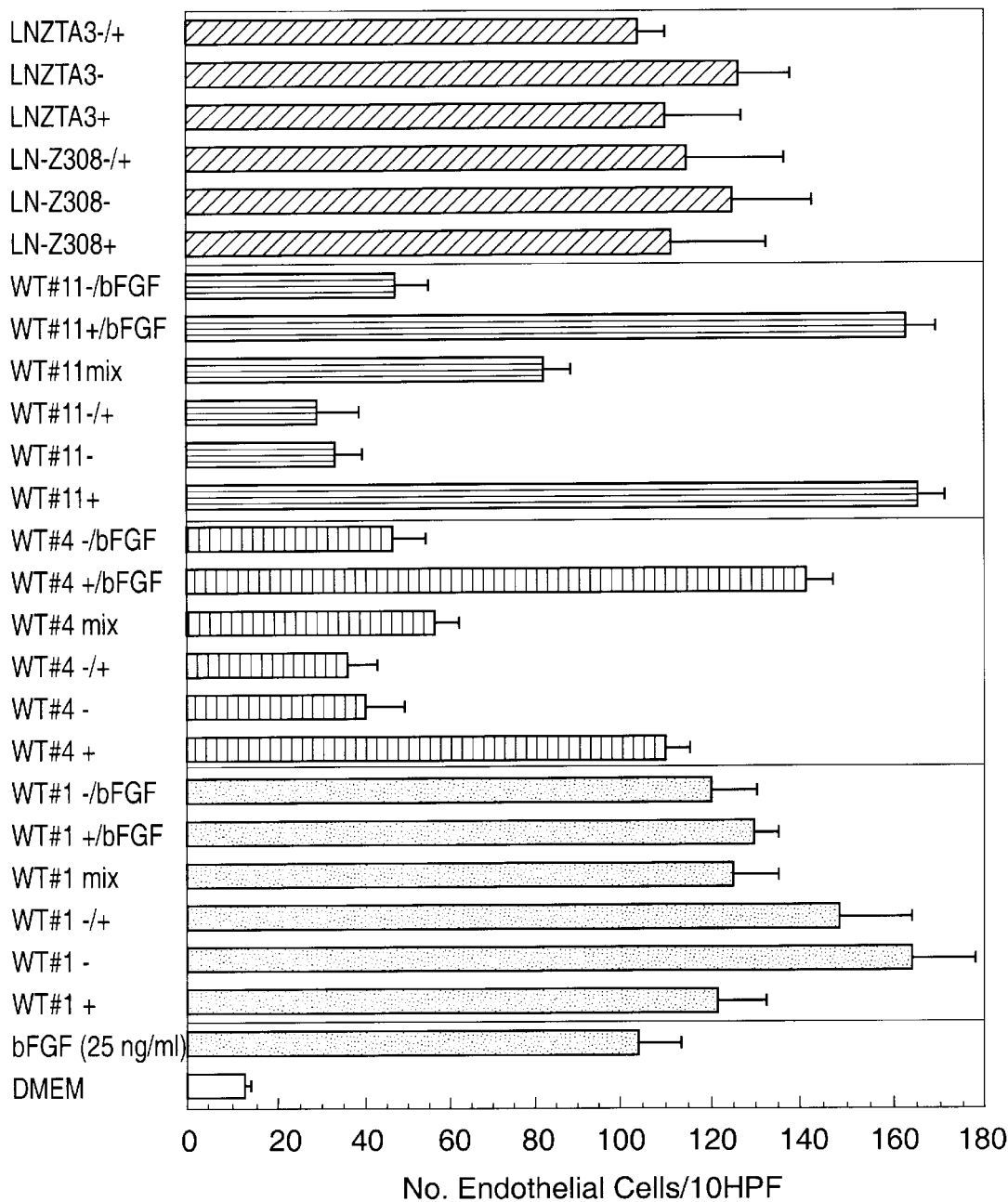
FIG. 2 summarizes a series of experiments studying in vitro endothelial cell migration. The total number of migrated cells per well were determined in 10 high power fields ("HPF"), and expressed as a percentage of migration observed with 25 ng/ml of bFGF. Cell lines LNZTA3 and LNZ-308 are controls. Cell line WT1, WT4 and WT11 are described in the application. The following explains the abbreviations.

FIG. 2 summarized these results. Reference should be made to the description of the FIGS., supra for interpretation of the abbreviations used.

As a final test to determine if the observed effect could be due to non-specific effects from the VP16 domain present in tTA, activities in the culture medium of clone WT1 in the presence (tTA inactivated), and absence (tTA activated) of tetracycline was studied. The tTA activation did not alter migration.

EXAMPLE 5

The activity of the conditioned medium was then tested in an in vivo system. Conditioned media, prepared as described supra, were mixed with HYDRON, the resultant pellets were implanted into rat corneas. The rat cornea assay of Rastinejad et al., Cell 56: 345–355 (1989) incorporated by reference in its entirety, was used. The assay is an accepted approach for determining in vivo angiogenesis and results obtained thereby are readily transferable to other in vivo systems.

In these experiments, the materials used included bFGF (25 ng per pellet), and conditioned medium from clones WT1, WT4, and WT11, which had been grown in the presence of tetracycline (1 ug/ml), and in its absence.

The results are presented in FIGS. 3A–3H. In FIG. 3A, a 21× magnification of a colloidal carbon perfused cornea 7 days after implantation of a HYDRON pellet containing WT1 conditioned medium, from induced and non-induced cells is shown. Neovascularization is evident.

In FIGS. 3C-D, results from pellets which contained concentrated conditioned medium from WT11 either induced (top) or not (bottom) for p53 expression are shown. A dramatic reduction in the number of capillary sprouts and loops is evident when the induced cell conditioned medium was used. Results when induced WT4 conditioned medium was used were similar even in the presence of bFGF (FIGS. 3G-H). Note, however, the high degree of vascularization when wt p53 was not induced.

In FIGS. 3E-F, perfused corneas are shown where pellets containing concentrated conditioned medium of WT11 prepared in the presence, and absence of tetracycline were used in the lower panel, conditioned medium from induced cells was mixed with bFGF. The cornea were scored as positive for angiogenesis, but the induced capillary network is much less dense than that of the control (FIGS. 3A-B), suggesting partial inhibition.

The results show that upon WTp53 induction, the neovascularization was strongly inhibited, with no positive response being found with WT11 (0/5) and only one positive with WT4 (1/5). Table 2 also summarizes these results, and follows.

TABLE 2

Inhibition of Corneal Nerovascularization by Wt p53

| Conditioned Media (5 μg protein per pellet) | Corneal Neovascularization Proportion of Positive Responses (%) |
|---|---|
| Controls |  |
| DME + 0.1% BSA | 0/3 (0) |
| bFGF (50 ng) | 3/3 (100) |

TABLE 2-continued

Inhibition of Corneal Nerovascularization by Wt p53

| Conditioned Media (5 μg protein per pellet) | Corneal Neovascularization Proportion of Positive Responses (%) |
|---|---|
| WT #1 | |
| WT #1 + | 4/4 (100) |
| WT #1 − | 4/4 (100) |
| WT #1 −/+ | 4/4 (100) |
| WT #1 mix | 3/3 (100) |
| WT #1 + (+ bFGF) | 4/4 (100) |
| WT #1 − (+ bFGF) | 3/3 (100) |
| WT #4 | |
| WT #4 + | 4/4 (100) |
| WT #4 − | 1/5 (20) |
| WT #4 −/+ | 0/5 (0) |
| WT #4 mix | 3/5 (60) |
| WT #4 + (+ bFGF) | 4/4 (100) |
| WT #4 − (+bFGF) | 1/5 (20) |
| WT #11 | |
| WT #11 + | 4/4 (100) |
| WT #11 − | 0/5 (0) |
| WT #11 −/+ | 0/5 (0) |
| WT #11 mix | 3/5 (60) |
| WT #11 + (+ bFGF) | 4/4 (100) |
| WT #11 − (+ bFGF) | 1/4 (25) |
| LNZ | |
| LNZ - 308 + | 3/3 (100) |
| LNZ - 308 − | 3/3 (100) |
| LNZ - TA3 + | 2/2 (100) |
| LNZ - TA3 − | 3/3 (100) |

EXAMPLE 6

As a final control, experiments were carried out to determine if the inhibitory effect was eliminated if p53 were mutated. Experiments were carried out in accordance with examples 1–4 with mutated forms of p53 being used. Specifically, p53 proteins mutated at codon 248 (Arg to Trp) or at codon 273 (Arg to His) were used. The angiogenic response obtained was identical to that obtained with the parental conditioned medium, in all cases.

EXAMPLE 7

A further series of experiments was carried out so as to further characterize the angiogenesis inhibiting factor of the invention.

Samples of cell line WT4 and WT11(derived from the human glioblastoma cell line LN Z308, referred to supra) were grown, as described supra, in the presence (tet+) or absence (tet⁻) of tetracycline. Conditioned media, described supra, were prepared also as described, and were then subjected to one of the following: (i) contact to a heparin/ agarose column; (ii) treatment with pronase; (iii) heating to 100° C. for 10 minutes; (iv) treatment under acidic conditions (pH 2.0); (v) treatment under alkaline conditions (pH 12.0). The resulting materials were then tested in an endothelial cell migration assay, as described in example 4, supra.

Tables 3 and 4 summarize these results. The values, presented in the "mean" and "std" columns, refer to endothelial cells migrating across the membrane toward the chemotactic stimulus provided by the conditioned media.

The results in Table 3, lines 7–10, show that the active factor does not bind to heparin-agarose, a property which distinguishes it from most angiogenic molecules. Moving to table 4, lines 2–4 show that the factor must be a protein, as pronase destroys its activity. The values in lines 2, 5 and 6 show that it is heat stable, in that the angiogenic activity of tet+, uninduced cells was inhibited, even after treatment of the conditioned media at 100° C. for 10 minutes. Moving to lines 7–10 of Table 4, the inhibitor activity is destroyed by both acid and base. The sum total of properties distinguishes the GD-AIF molecule from all other antiangiogenic molecules known to the art.

TABLE 3

| # | Sample name | mean | std |
|---|---|---|---|
| 1 | DMB + 0.1% BSA | 10.67 | 1.53 |
| 2 | bFGF (50 ng/ml) | 79.00 | 4.36 |
| 3 | tet+ (10/μg/ml) | 201.00 | 14.73 |
| 4 | tet+ (10/μg/ml) + bFGF (50 ng/ml) | 199.33 | 1.53 |
| 5 | tet⁻ (10/μg/ml) | 49.00 | 8.19 |
| 6 | tet+ (10/μg/ml) + bFGF (50 ng/ml) | 47.33 | 3.51 |
| 7 | tet+ heparin unbound fraction (10/μg/ml) | 80.67 | 6.43 |
| 8 | tet+ heparin unbound fraction (10/μg/ml) + bFGF (50 ng/ml) | 86.67 | 10.26 |
| 9 | tet⁻ heparin unbound fraction (10/μg/ml) | 12.67 | 2.52 |
| 10 | tet⁻ heparin unbound fraction (10/μg/ml) + bFGF (50 ng/ml) | 24.67 | 5.69 |
| 11 | tet+ heparin bound (10/μg/ml) | 125.00 | 5.57 |
| 12 | tet+ heparin bound (10/μg/ml) + bFGF (50 ng/ml) | 131.33 | 10.60 |
| 13 | tet⁻ heparin bound (10/μg/ml) | 20.33 | 4.16 |
| 14 | tet⁻ heparin bound (10/μg/ml) + bFGF (50 ng/ml) | 78.67 | 2.08 |

Note:
1). These are chemotaxis data, scoring a number of migrated bovine capillary endothelial cells.
2). bFGF used as a chemoattractant.
3). Similar results if VEGF used as a chemoattractant.

TABLE 4

| # | Sample name | mean | std |
|---|---|---|---|
| 1 | DMEM + 0.1% BSA | 84.1 | 8.43 |
| 2 | tet+ (5 μg/ml) | 270.9 | 33.8 |
| 3 | tet⁻ (20 μg/ml) pronase treated | 25.2 | 2.13 |
| 4 | tet⁻ (20 μg/ml) pronase treated + tet+ (5 μg/ml) | 290.5 | 36.8 |
| 5 | tet⁻ (20 μg/ml) heated treated (100° C., 10 min.) | 29.7 | 3.75 |
| 6 | tet⁻ (20 μg/ml) heated treated (100° C., 10 min.) + tet+ (5 μg/ml) | 31.9 | 5.31 |
| 7 | tet⁻ (20 μg/ml) pH 2.0 treated | 27.8 | 2.47 |
| 8 | tet⁻ (20 μg/ml) pH 2.0 treated + tet+ (5 μg/ml) | 259.1 | 24.7 |
| 9 | tet⁻ (20 μg/ml) pH 12.0 treated | 26.8 | 2.93 |
| 10 | tet⁻ (20 μg/ml) pH 12.0 treated + tet+ (5 μg/ml) | 245.6 | 31.7 |

Note:
1). These are chemotaxis data, scoring number of migrated human microvascular endothelial cells.
2). tet+ conditioned medium used as a chemoattractant which contains several angiogenic factors such as bFGF and VEGF.

The foregoing experiments describe the identification of an angiogenesis inhibiting factor. In one, non-limiting embodiment, it is produced by glioblastoma cells. Hereinafter, the factor is referred to as "GD-AIF"for "glioblastoma derived, angiogenesis inhibiting factor". This material inhibits both bFGF and glioma derived angiogenic factors, and acts directly upon endothelial cells. In addition, its production appears to be induced by wild type p53 protein, and not by mutant forms of this suppressor protein.

This GD-AIF does not bind to heparin, is resistant to heat (100° C., 10 minutes treatment), and is sensitive to both acid (pH 2.0), and alkaline (ph 12.0) treatment, which distinguishes it from all other known antiangiogenic factors.

Two cell lines, WT4 and WT11 have been produced which contain the wild type p53. The cell lines contain a p53 encoding sequence which is under the control of tetracycline, i.e., p53 is produced in the absence of the antibiotic, and is not, in its presence. The cell lines derive from parental glioblastoma cell line LN-Z308, and have been deposited at the American Type Culture Collection 12301 Parklawn Drive, Rockville, Md. 20852, on Feb. 1, 1994 and have been accorded Accession Numbers CRL 11543 (WT4) and CRL 11544 (WT11), respectively.

One aspect of the invention involves the GD-AIF molecule itself, either in isolated form, or as part of a conditioned medium or cell lysate. These materials, containing the GD-AIF, are produced by culturing a cell capable of producing the molecule, in the presence of wild type p53. The wild type p53 may be added in the form of the protein per se or the cell lines which are capable of producing the factor, such as glioblastoma cells, may be transfected with WTp53 encoding sequences. Most preferably, these sequences are operably linked to promoters or other sequences which are regulatable, such as the tetracycline regulatable regulatory elements described herein.

In practice, one may obtain the GD-AIF in vitro by culturing the transfected cells, or cells grown to be induced for WTp53. One may also produce the material in vivo, however, by introducing WTp53 coding sequences, materials which mimic p53 action, coding sequences corresponding to downstream effectors of the p53 pathway, materials which mimic the properties of the downstream effectors, or any agent which will induce and/or stimulate the production of wild type p53, such as those discussed supra, to a targeted site where angiogenesis inhibition is desirable. The methodologies for such targeted therapies are well known, including retroviral transfer, other DNA/RNA based delivery systems, complexes of glioblastoma specific antibodies and carriers of the WTp53 gene (such as liposomes), and so forth. This methodology eliminates the need to produce the GD-AIF in vitro, by forcing target cells to produce it. Such targeting is desirable in any of the situations such as those set out in the "BACKGROUND AND PRIOR ART" section where inhibition of angiogenesis is desirable. Of course, direct application of the GD-AIF, if produced in vitro is also possible and desirable.

The GD-AIF molecule, as analyzed by sizing filters, appears to have a molecular weight of approximately 100 kilodaltons. It is a material which is inactivated by both base and acid. The only other known factor with properties analogous to those recited for GD-AIF, is hamster thrombospondin, which is a material located in extracellular matrix and is not normally found in the culture medium of cells to any extent. Further, the presence or absence of p53 in WT4 or WT11 cells had no effects on the levels of the material, as determined in an in vitro, immunoprecipitation assay using antibodies to thrombospondin. "GD-AIF" should be recognized simply as a convenient name for the factor, and is not to be taken as indicating that glioblastoma is the only tissue, cell or tumor type capable of producing the material. It is a convention in the art to sometimes name a factor after the first source for it (e.g., "platelet derived growth factor, placental derived endothelial cell growth factor, fibroblast growth factor"), but the factor is also produced by many other sources. Thus, "GD-AIF" does not limit the factor to production by glioblastoma and, also, cells which produce the factor may, but need not be, glioblastoma.

Other aspects of the invention will be clear to the skilled artisan, and need not be set forth here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated angiogenesis inhibiting factor which (i) is resistant to heating at 100° C. for 10 minutes, (ii) is sensitive to acid at pH 2.0, (iii) is sensitive to alkali at pH 12.0, (iv) does not bind to heparin, (v) has an apparent molecular weight of about 100 kd as analyzed by sizing filters (vi) does not bind to thrombospondin specific antibodies, (vii) is not thrombospondin, and (viii) can be induced by p53 expression wherein said factor inhibits angiogenesis.

* * * * *